United States Patent [19]

Sakuraba et al.

[11] Patent Number: 4,847,910
[45] Date of Patent: Jul. 11, 1989

[54] AUTOMATIC CELL SAMPLE CLASSIFYING APPARATUS

[75] Inventors: Shinichi Sakuraba; Hajime Matsushita, both of Katsuta; Masaaki Kurimura, Ibaraki, all of Japan

[73] Assignee: Hitachi, Ltd., Tokyo, Japan

[21] Appl. No.: 67,003

[22] Filed: Jun. 29, 1987

[30] Foreign Application Priority Data

Jun. 30, 1986 [JP] Japan .................................. 61-153920

[51] Int. Cl.$^4$ ............................................. G06K 9/00
[52] U.S. Cl. .......................................... 382/6; 356/39; 364/413.08; 382/17
[58] Field of Search .................. 382/6, 17; 356/39, 40, 356/41; 364/416; 424/3

[56] References Cited

U.S. PATENT DOCUMENTS

| | | | |
|---|---|---|---|
| 3,499,047 | 12/1976 | Green | 382/17 |
| 3,851,972 | 12/1974 | Smith et al. | 356/39 |
| 3,899,297 | 8/1975 | Hirsch et al. | 424/3 |
| 3,916,205 | 10/1975 | Kleinerman | 424/3 |
| 4,125,828 | 11/1978 | Rosnick et al. | 382/17 |
| 4,191,940 | 3/1980 | Polcyn et al. | 382/17 |
| 4,479,242 | 10/1984 | Kurata | 382/17 |
| 4,562,593 | 12/1985 | Ooe et al. | 382/6 |

Primary Examiner—Leo H. Boudreau
Assistant Examiner—Joseph Maniuso
Attorney, Agent, or Firm—Fay, Sharpe, Beall, Fagen, Minnich & McKee

[57] ABSTRACT

A stain discriminating apparatus in which light rays having at least light component having a wavelength in a predetermined range are projected to a cell sample to discriminate the staining method by which the cell sample has been stained on the basis of the light intensity of the light component transmitted through the sample and having the wavelength (530 nm) in the predetermined range. An automatic cell sample classifying apparatus in which a plurality of cell sample slides are sequentially fed to the stain discriminating apparatus is used to determine the staining method by which the cell samples have been stained, respectively. One of the examination/classification programs previously stored in a memory is read out according to the staining method as discriminated and the cell samples are processed in accordance with the program as read out.

5 Claims, 6 Drawing Sheets

AUTOMATIC CELL SAMPLE CLASSIFYING APPARATUS

BACKGROUND OF THE INVENTION

The present invention generally relates to an automatic cell sample classifying apparatus and more particularly to the automatic cell sample classifying apparatus including an automatic stain discriminating apparatus for discriminating a staining method which has been adopted in staining a given one of plural cell samples stained by respective predetermined different staining methods.

In order to automatically examine and classify a number of cell samples stained by respective different staining methods by means of an automatic cell sample classifying apparatus, it is necessary to discriminate or determine in precedence which of the different staining methods has been employed in staining a given one of the plural cell samples. However, there has heretofore been known no apparatus capable of discriminating the staining methods. Consequently, in the automatic cell sample classifying apparatus such as disclosed, for example, in U.S. Pat. No. 3,851,972 issued on Dec. 3, 1974 to Smith et al, entitled "Automatic Method and System for Analysis and Review of A Plurality of Stored Slides", and co-pending U.S. patent application Ser. No. 938,964 entitled "Cellular Analysis System", a large number of cell samples are preceedingly classified through manual procedure for each of the staining methods, wherein the samples stained by the same method are processed by preparing an examination/classification program appropriate to that staining method. When the cell samples stained by another method are to be processed, the examination and classification program must be correspondingly changed. Alternatively, the cell samples stained by the same method may be accommodated in a same cassette, wherein examination/classification programs are prepared for the cassettes in correspondence to the staining methods applied to the sample slides accommodated in the cassettes, respectively.

In the case of the system disclosed in the aforementioned U.S. Patent Application, each cassette is attached with a mark indicating the staining method by which the cell sample slides contained in the cassette have been stained, and the mark is read by an automatic classification apparatus to thereby set automatically the examination/classification program pertinent to the staining method indicated by the mark. As an alternative, each cell sample may be affixed with a mark indicating the staining method applied to that cell sample, which mark is then read by the automatic classification apparatus. In any case, however, accommodation of the cell samples stained by the same method in each cassette as well as checking for assuring correct indication of staining methods by the marks must be performed through manual procedure.

SUMMARY OF THE INVENTION

It is therefore an object of the present invention to provide a stain discriminating apparatus capable of optically discriminating the staining method by which a given one of cell samples has been stained by taking advantage of certain physical characteristics of the cell sample.

Another object of the present invention is to provide an automatic cell sample classification apparatus equipped with the stain discriminating apparatus for determining which of plural different staining methods has been adopted in staining a given one of the cell samples.

In view of the above objects, there is provided according to an aspect of the present invention a stain discriminating apparatus which includes means for projecting light rays containing at least one component having a wavelength in a predetermined range, and means for determining the staining method adopted in staining a given cell sample from the light intensity level of the light ray transmitted through the given cell sample.

According to another aspect of the present invention, there is provided an automatic cell sample classifying apparatus which comprises a loader accommodating cell sample slides each of which is stained by one of the plural predetermined staining methods, an examination station, a carrier for extracting the cell sample slides sequentially from the loader and transporting the extracted sample slides to the examination station along a predetermined path, a means disposed in a region located in the vicinity of the transportation path inclusive of the examination station for producing a light intensity signal indicative of the luminous intensity of at least a light component transmitted through a slide passing the transportation path and having a wavelength in a predetermined range, a discriminator for deriving a discriminating signal on the basis of the light intensity signal, which signal indicates one of the plural staining methods by which a given one of the cell samples has been stained, a means for obtaining a microscopic image of the cell sample of a sample slide placed in the examination station, and a processor for examining and classifying the cell samples of the sample slides by processing the microscopic image in accordance with an examination/classification program determined by the discriminating signal, respectively.

DESCRIPTION OF THE PREFERRED EMBODIMENTS

Figure 1:
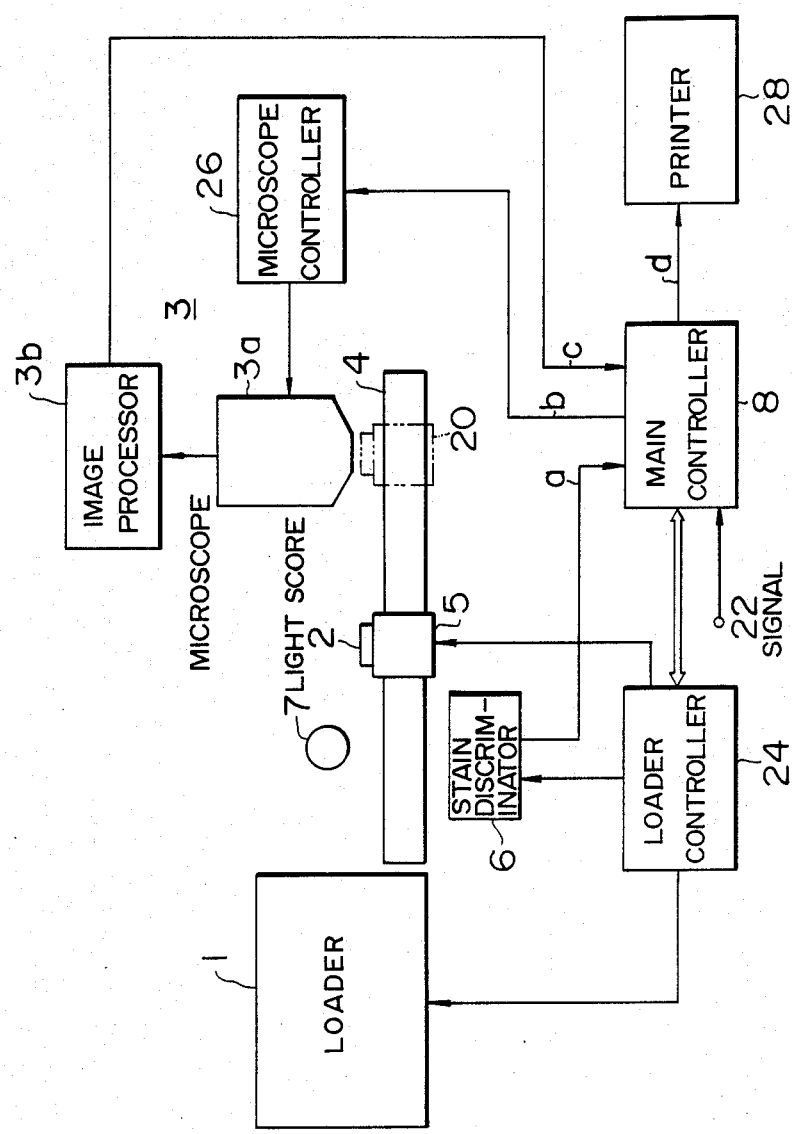
FIG. 1 is a view showing a general arrangement of an automatic cell sample classification apparatus according to an embodiment of the present invention.

Now, the invention will be described in conjunction with an exemplary embodiment thereof by referring to the drawings on the assumption that the invention is applied to an apparatus for automatically classifying blood cell samples.

FIG. 1 is a view showing schematically in a block diagram a general arrangement of the automatic cell sample classification apparatus according to an embodiment of the invention. In the figure, a reference numeral 1 denotes a slide loader for loading a large number of cell sample slides which have been stained by staining methods selected in accordance with the intended cellular examinations or analyses. The loader 1 usually accommodates therein 12 cassettes each of which in turn contains 25 cell sample slides. Disposed between the abovementioned loader 1 and an examination station 20 is a slide transporting rail 4 on which a carrier 5 is slidably mounted. The loader 1 is preferably mounted rotatably about a center shaft (not shown), wherein 12 cassettes accommodated within the loader 1 are disposed substantially coaxially with the center shaft so that any given one of the cassettes can be positioned in opposition to the carrier 5 by indexing the loader 1 to a corresponding angular position. Further, the loader 1 is mounted movably stepwise along the shaft in the vertical direction (i.e. upwardly and downwardly) so that the slides contained in the cassette located in opposition to the carrier 5 can be sequentially indexed at the slide extracting position. The slide 2 located at the slide extracting position is taken out from the cassette and transported to the examination station 20 by means of the carrier 5 to be subsequently examined with the aid of an examining system 3 including a microscope 3a, , as described hereinafter. The slide 2 that has undergone the examination is returned to the original position within the associated cassette by means of the carrier 5. Thereafter, the loader 1 is driven upwardly by one step, wherein the next slide is extracted to undergo examination through the similar procedure as mentioned above and finally returned to the original position within the cassette. When examination of all the slides contained in one cassette has been completed, the loader 1 is indexed to the angular position at which the next cassette is positioned in opposition to the carrier 5. Additionally, the loader 1 is moved downwardly to the position where the slide contained in the cassette at the topmost stage is positioned opposite to the slide extracting position. In this manner, all the cell sample slides accommodated within the loader 1 are sequentially examined to be subsequently classified in dependence on the results of the examination. Operation of the loader 1 and the carrier 5 described above is controlled by a loader controller 24 which is operated in synchronism with the operation of the examining system 3 in response to a signal supplied from a main controller 8 which in turn is activated by a start signal 22 generated through manual operation. Since this type of control mechanism is known as disclosed in the aforementioned co-pending U.S. patent application No. 938,964, any further description will be unnecessary.

The examination system 3 includes a microscope unit 3a equipped with a TV camera, microscope controller 26 and an image processor 3b which is so designed as to process signals representing the microscopic images of individual cell samples generated by the microscope unit 3a for deriving data indicating specific characteristic features selected in dependence on the staining methods applied to the cell samples. When each of the slides has reached the examination station 20, the microscope controller 26 drives the microscope unit 3as with instructions b derived from the main controller 8 so as to scan two-dimensionally the slide set at the examination station in a manner as shown in the afore-mentioned co-pending U.S. application thereby catching an image of the stained cells contained in the slide in a field of the microscope's view. Since the processing procedure performed by an image processor differs from one to another staining method as applied, it is necessary to get knowledge as to which staining method has been applied to a cell sample to be examined in precedence to the start of the processing operation. To this end, a stain discriminator 6 is disposed in the vicinity of the path along which the sample slide 2 is transported from the loader to the examination station 20 in the case of the illustrative embodiment shown in FIG. 1. In the course of studies and experiments conducted by the inventors in an effort to develop an automatic stain discriminating system for the stained cell samples, it has been observed that the light absorption characteristics of the stained cell samples to the light component of a particular wavelength differ from one to another sample in dependence on the applied staining methods. The present invention is based on this fact.

Figure 2:
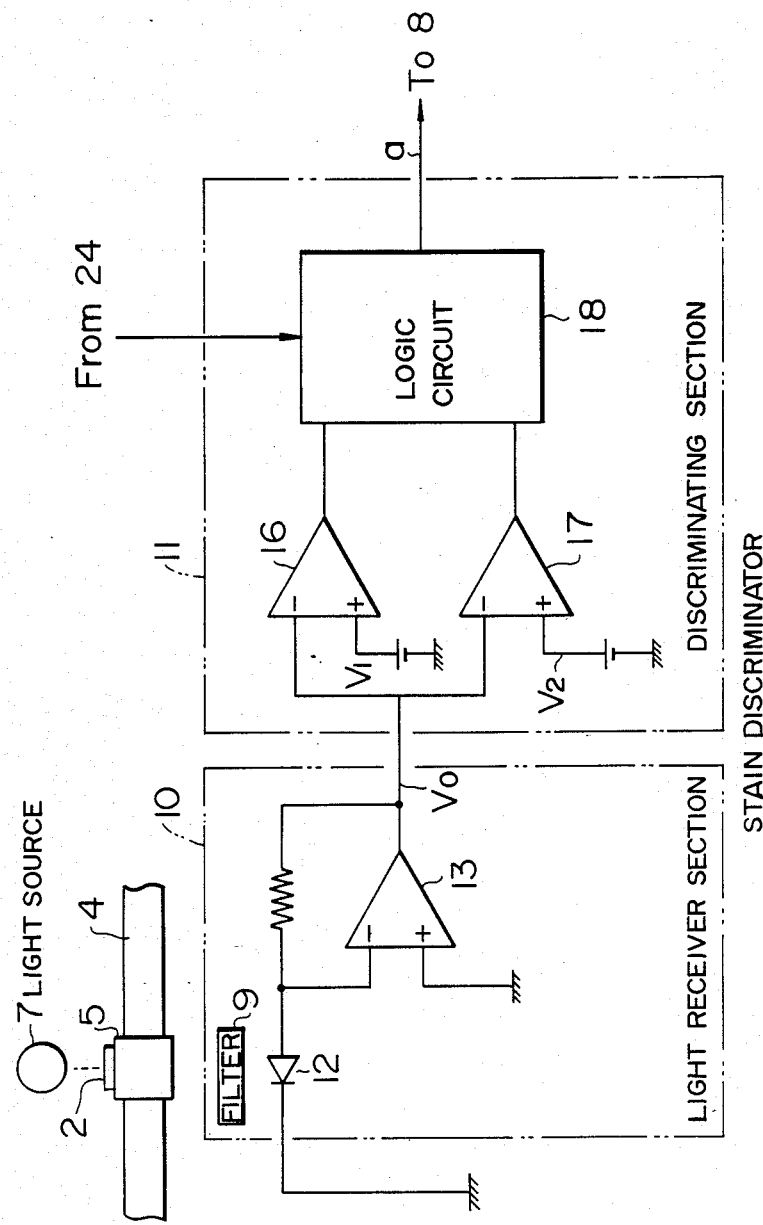
FIG. 2 is a view showing in a block diagram a circuit arrangement of a staining discrimination apparatus employed in the apparatus shown in FIG. 1.

Referring to FIG. 2, a stain discriminator according to the present invention generally denoted by a numeral 6 in FIG. 1 includes a light source 7 disposed on one side of the slide transportation rail 4 for illuminating a cell sample slide carried by the carrier 5 movable on the rail 4, a light receiving section 10 for receiving the light transmitted through the cell sample slide 2 carried by the carrier 5 and producing an output signal indicating light intensity of the specific wavelength component and a discriminating section 11 for discriminating the staining method on the basis of the information of the output signal from the light receiving section 10. Parenthetically, it should be mentioned that the carrier 5 is implemented in the form of a hollow cylinder to ensure that the light rays emitted by the light source 7 and transmitted through the slide 2 can reach the light receiving section 10 without loss. The light receiving section 10 includes a filter 9 for passing therethrough only a predetermined wavelength component of the light rays emitted by the light source 7, a photo-sensitive element 12 disposed so as to receive the light having passed through the filter 9, and an opto-electronic converter circuit composed of an operational amplifier 13 for producing a voltage signal V0 having an amplitude varying in proportion to the current flowing through the photo-sensitive element 12. Since the current flowing through the photo-sensitive element 12 is a function of the light intensity of the light rays impinging onto the element 12, the output voltage V0 reflects the light intensity of the particular wavelength component of the light illuminating the photo-sensitive element 12 and hence the light intensity of the light component having transmitted through the cell sample 2. The discriminating section 11 includes comparators 16 and 17 for comparing the abovementioned output voltage V0 inputted thereto with reference voltages V1 and V2, respectively, and a logic circuit 18 for processing the output signals of the comparators 16 and 17. The levels of the reference voltages V1 and V2 are so selected that the output signal of the logic circuit 18 indicates the type of the method which has been applied in staining the cell sample to be examined. For having a better understanding, elucidation will be made below on the various staining methods adopted in conjunction with the classification of blood cells and the light absorption characteristics of the blood cells.

Figure 4:
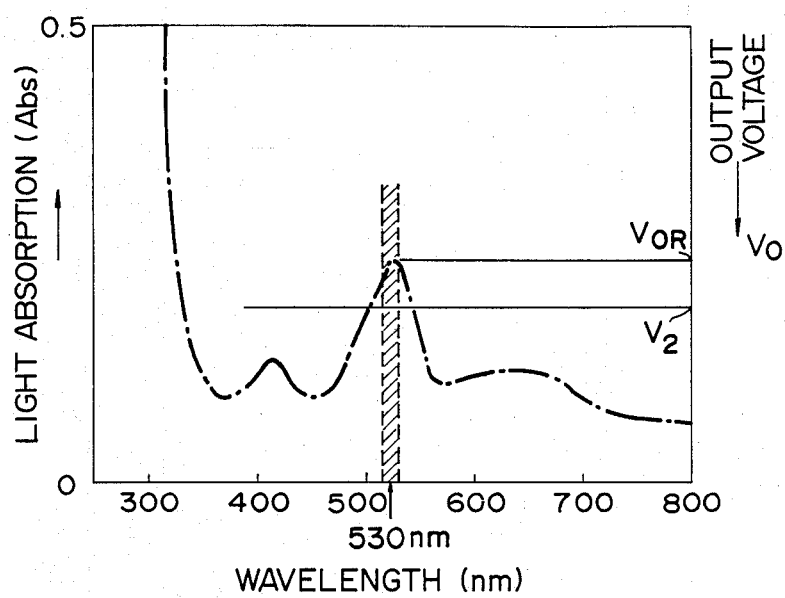
FIGS. 4 and 5 are views for graphically illustrating light absorption characteristics of cell samples stained by different staining methods.
Figure 5:
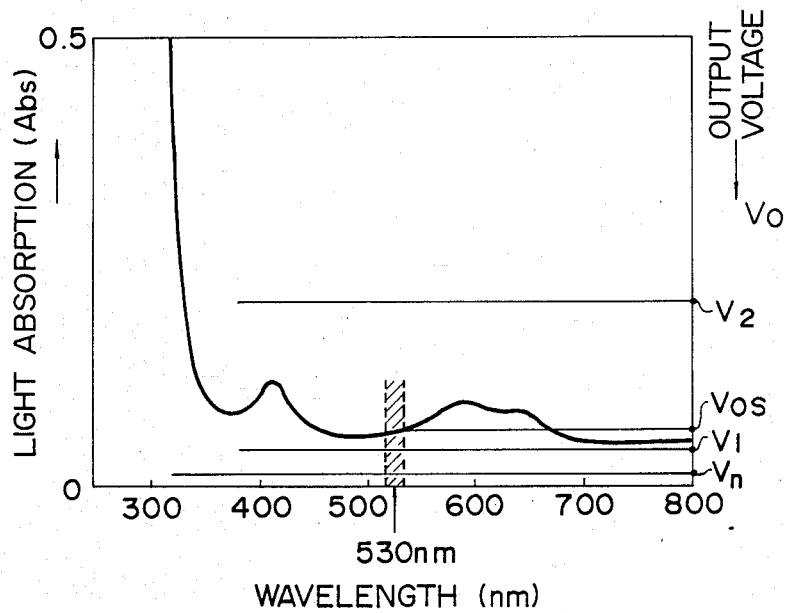

The blood cell classification adopted ordinarily is directed primarily to the classification of white blood cells (leucocytes), red blood cells (erythrocytes) and reticrocytes. The staining method applied thereto however differs depending on the sort of the cells to be classified. For example, Romanowsky staining method (May-Grünwald-Giemsa staining method) is adopted for classification of the white blood cells and the red blood cells, while spravital staining method (new methylen blue staining method) is employed for classification of reticrocytes. FIG. 4 shows a light absorption characteristic curve obtained from a sample stained by the Romanowsky method, and FIG. 5 shows a light absorption characteristic curve obtained from a sample stained by the spravital staining method. In these figures, wavelength is taken along the abscissa (in nm) with the light absorption being taken along the ordinate (in absolute unit). From the comparison of the light absorption characteristic curves, it will be seen that very significant difference is found in the light absorption around the wavelength of 530 nm between the sample stained by the Romanowsky method and the sample stained by the spravital method. Accordingly, it is possible to discriminate the samples of white blood cells and red blood cells from that of reticrocytes on the basis of the degree of light absorption at the wavelength in the vicinity of 530 nm.

In view of the foregoing, the filter 9 of the light receiving section 10 is so designed that only the light rays having the wavelength around 530 nm (e.g. 530 nm+5 nm) can pass therethrough. Since the output voltage V0 of the light receiving section 10 is in proportion to the light intensity of the light transmitted through the cell sample, each of the curves shown in FIGS. 4 and 5 represents also the output voltage V0 of the light receiving section 10. In this connection, it will be noted that the voltage values are taken along the righthand ordinate in the decending order in FIGS. 4 and 5, respectively. Further, in these figures, the output voltage of the light receiving section 10 produced for the cell sample stained by the Romanowsky method is represented by VOR, while the output voltage 10 for the cell sample stained by the spravital method is represented by VOS. Since the voltages VOR and VOS can vary within certain ranges, the reference voltage V2 (refer to FIG. 2) is selected to be lower than the expected maximum value of the voltage VOR (the voltage V2 is constantly lower than the voltage VOR as shown in FIG. 4) and higher than the expected minimum value of the voltage VOS (the voltage V0 is always higher than VOR as shown in FIG. 5). On the other hand, the other reference voltage V1 is selected higher than the expected maximum value of the voltage VOS and lower than the output voltage V0 obtained for the blank slide containing no cells. This voltage V0 is referred to as the no-sample voltage and designated by Vn. On these conditions, when the output voltage V0 of the light receiving section 10 is $$V0 < V2 \tag{1}$$

it is then decided that the cell sample under observation is the one stained by the Romanowsky method. On the other hand, when $$V2 < V0 < V1 \tag{2}$$

it is determined that the cell sample was stained by the spravital method. The comparators 16 and 17 and the logic circuit 18 of the discriminating section 11 shown in FIG. 2 serve to decide which of the ranges given by the expressions (1) and (2) the output voltage V0 falls within. The discriminating signal a of the logic circuit 18 may be, for example, a binary signal of two bits and assumes "1, 1" when the voltage V0 is in the range defined by the expression (1), indicating that the sample cell under illumination is the one stained by the Romanowsky method. On the other hand, when the discriminating signal is "1, 0", it is indicated that the sample cell was stained by the spravital method. In the case of a no-sample slide, the discriminating signal Vn is "0, 0", Operation timing of the logic circuit 18 is so controlled by a signal supplied from the loader controller 24 that the logic circuit 18 operates in synchronism with the motion of the carrier 5. More specifically, at the time point when the carrier 5 has attained the position to traverse the path of the light beam projected to the light receiving section 10 from the light source 7, the loader controller 24 supplies a signal to the logic circuit 18 which responds thereto by holding the discriminating signal a derived from the output signal V0 of the light receiving section 10 and sends it to the main controller 8. The discriminating signal held by the logic circuit 18 is cleared simultaneously with the initiation of movement of the carrier 5 to transport the next slide to the examination station from the loader 1.

Figure 3:
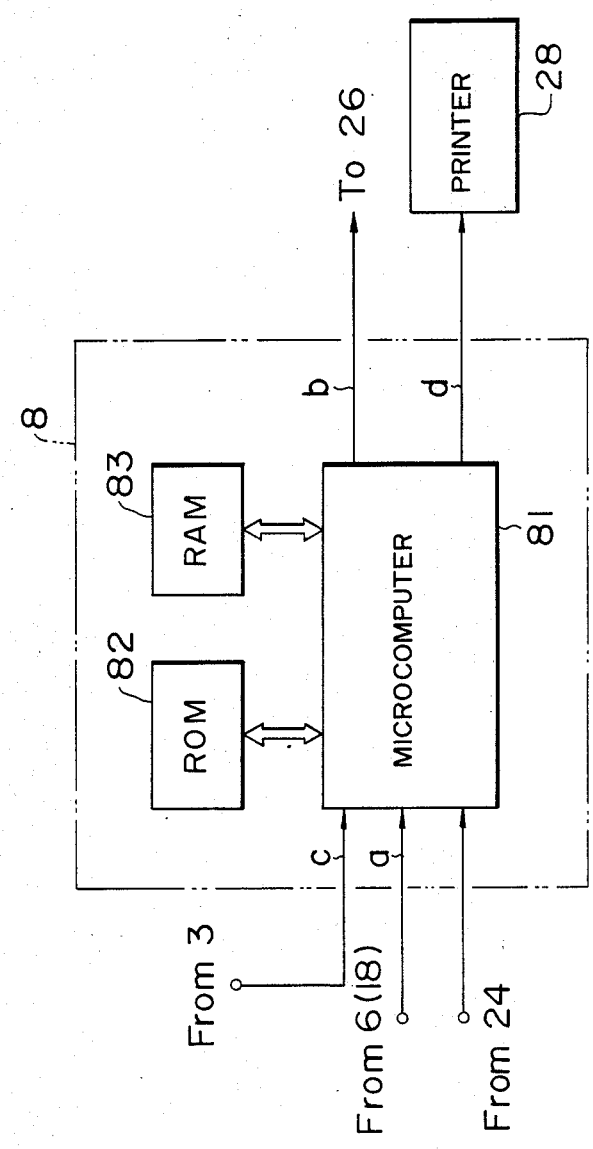
FIG. 3 is a block diagram showing a circuit arrangement of a central control unit employed in the apparatus shown in FIG. 1.
Figure 6:
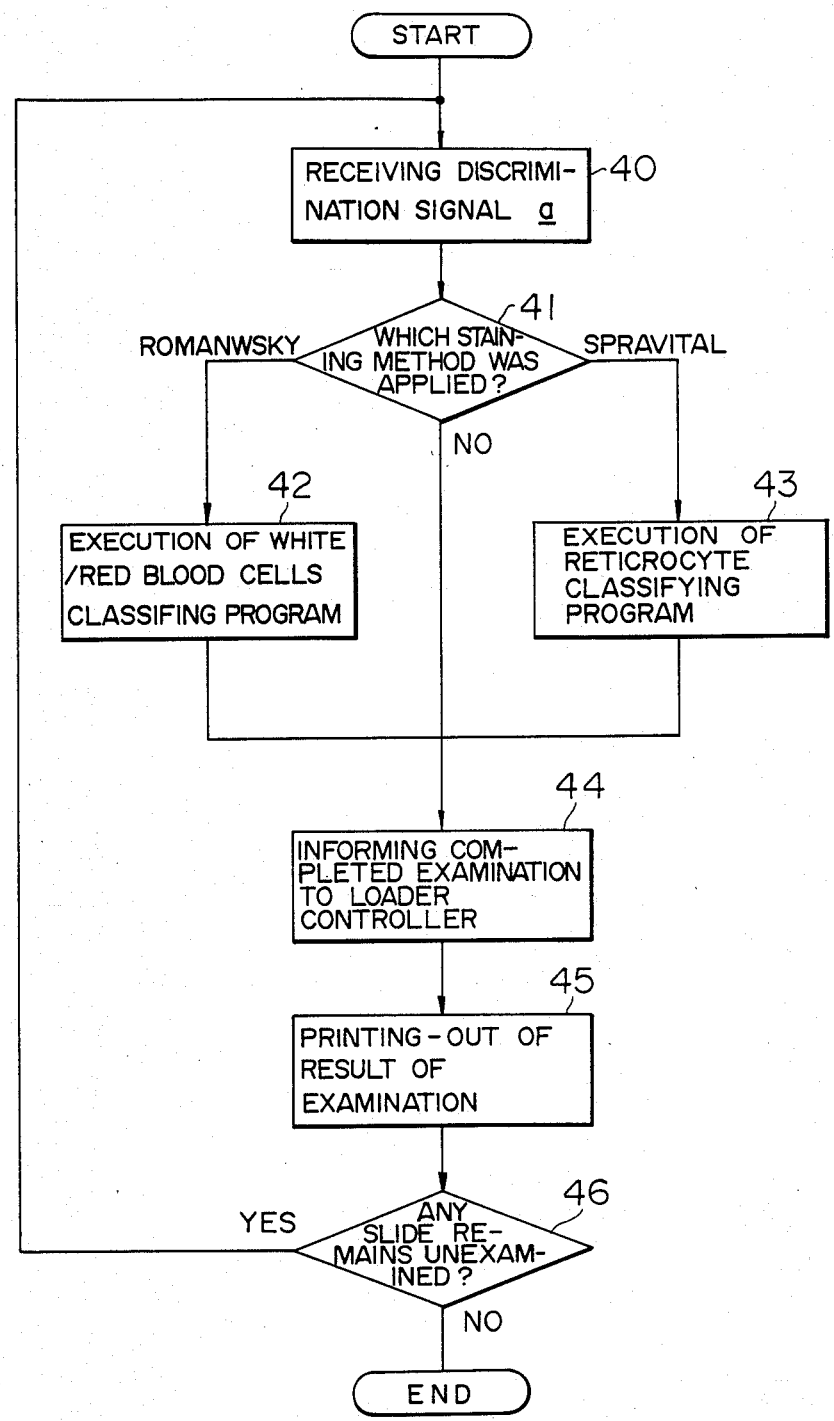
FIG. 6 shows a flow chart for illustrating procedure for processing a microscopic image of a cell sample.

As is shown in FIG. 3, the main controller 8 includes a microcomputer 81, a ROM 82 and a RAM 83. Various classification programs such as leucocyte/erythrocyte classification program and reticrocyte classification program are addressably stored in the ROM 82. Upon starting of operation, the microcomputer 81 first executes an initialization routine (not shown), being followed by the examination/classification procedure illustrated in FIG. 6. More specifically, at a step 40, the central control circuit 8 awaits the reception of the discriminating signal a from the stain discriminator 6. Upon reception of the signal a, it is determined at a step 41 which staining method is indicated by the signal a. When the Romanoswky staining method is indicated, the processing proceeds to a step 42 where the leucocyte/erythrocyte classification program is read out from the ROM 82 since the Romanowsky staining method is destined for classification of white and red blood cells. On the other hand, when the decision at the step 41 indicates the spravital staining method, the procedure proceeds to a since the spravital staining method is adopted for classification of the reticrocytes. Since these programs can be executed in the manner disclosed in co-pending U.S. patent application No. 938,964, further detailed description is omitted. Data resulting from execution of any classification program are stored in the RAM 83. Upon completed execution of the step 42 or 43, the procedure proceeds to a step 44 where a completed examination signal is supplied to the loader controller 22, being followed by a step 45. At this step 45, the data stored in the RAM 83 are printed out by a printer 28. In the meantime, the loader controller 24 supplied with the completed examination signal activates a series of carrier driving processes for returning the cell sample slide that has undergone the examination to the original position within the associated cassette and extracting and transporting the next cell sample slide to the examination station. These carrier driving processes are executed in parallel with the printing out operation of the printer 28. At a step 46 following the step 45, it is checked whether there remains any cell sample slides which are not yet examined. If so, the step 40 is regained to wait for the reception of the discriminating signal. Otherwise, the processing comes to an end.

It should be mentioned that when the discriminating signal a indicates other information than any particular staining method at a step 41 (such situation may take place, for example, when no stained cell samples are present in the slide), the procedure proceeds directly to the step 44. Under the circumstance, no data to be printed at the step 45 is present in the RAM 83. Accordingly, the process is immediately advanced to the step 46.

The foregoing description has been made on the assumption that the cell samples are stained by two types of staining methods. It should however be understood that the present invention can be readily applied to a case where three or more staining methods are adopted. By way of example, it is assumed that three staining methods A, B and C are adopted. On the assumption, when the cell sample stained by the method A exhibits a light absorption differing significantly from the cell sample undergone the staining B at a wavelength W1 while the sample stained by the method B has the light absorption remarkably different from that of the sample stained by the method C at a wavelength W2, it is possible to identify which of the three staining methods has been actually employed for a given cell sample by using two light beams having the wavelengths W1 and W2 and comparing the light absorption of that given cell sample for each of the wavelengths W1 and W2. The light source should preferably be so selected that the light intensity is constant at or in the vicinity of the wavelength selected for the discriminating processing. To this end, a halogen lamp may be used.

Figure 7:
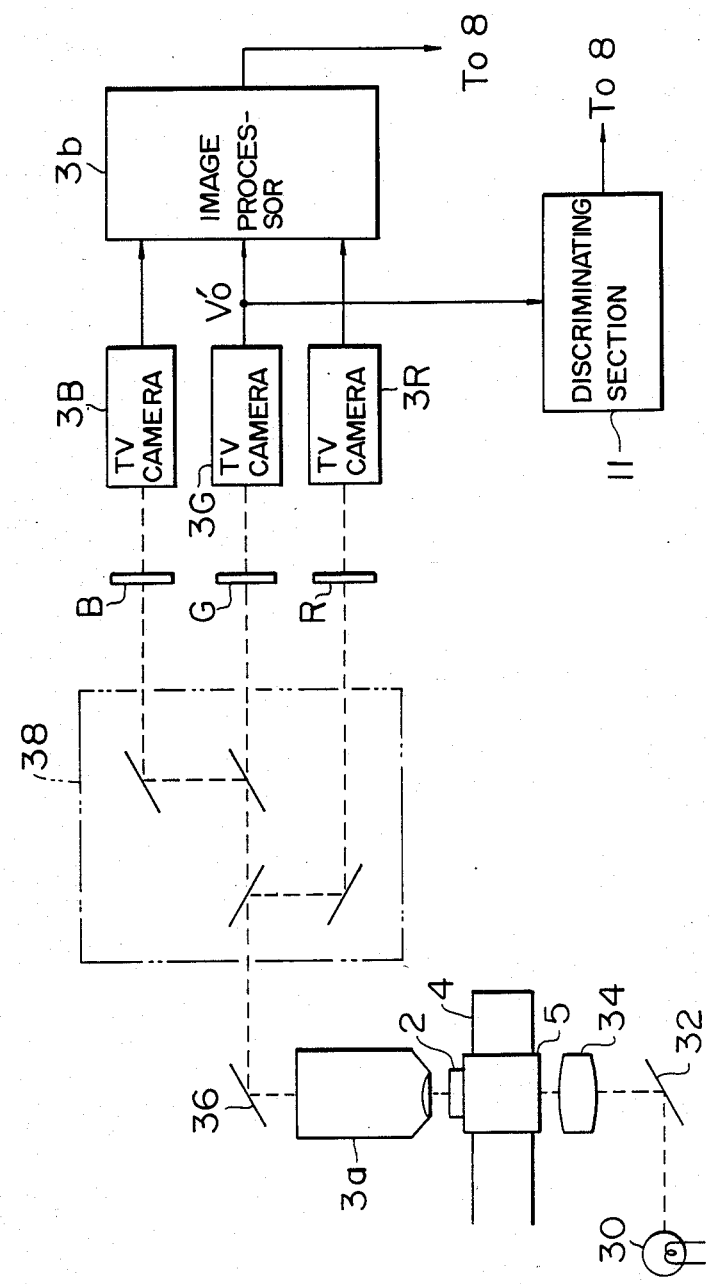
FIG. 7 is a view showing a general arrangement of an automatic cell sample classification apparatus according to another embodiment of the present invention.

Next, another embodiment of the invention will be described by referring to FIG. 7 in which same or like parts as those shown in FIGS. 1 and 2 are denoted by same reference numerals. It should however be noted that the television camera assumed to be incorporated in the microscope in the case of the system shown in FIGS. 1 is shown independently and thus the reference character 3a denotes only the microscope in the case of the embodiment shown in FIG. 7. Referring to this figure, reference character 30 denotes a light source, 34 denotes a condenser lens for collecting light rays emitted from the light source and reflected by the mirror 32, B, G and R denote blue, green and red filters, respectively, 3B, 3G and 3R denote TV cameras for deriving three color-separated image signals (i.e. blue, green and red image signals) from the color separated images obtained through the filters B, G and R, respectively, and 3b denotes an image processor for producing the data indicating particular characteristic features of a cell sample by processing the output signals from the TV cameras. Finally, reference numerals 36 and 38 denote sets of mirrors for dividing the light carrying an image of the cell sample as observed by the microscope 3a into three parts directed to the filters B, C and R, respectively. Although not clearly shown in FIG. 1, three TVs for three color images are incorporated in the microscope 3a in practical application. Accordingly, the apparatus shown in FIG. 1 may be regarded to have the same structure as the one mentioned above. The embodiment shown in FIG. 7 is based on the fact that the light ray after being transmitted through the green filter has a wavelength of about 530 nm. More specifically, since the color-separated signal V0' obtained from the green TV camera 3G corresponds to the output signal V0 of the light receiver section 10 shown in FIG. 2, this signal V0' is supplied to the discriminator 11 to be utilized in determining the type of the staining method applied to the cell sample. The structure of the discriminator circuit shown in FIG. 7 is basically the same as that of the circuit shown in FIG. 2 although some modifications will have to be made concerning the selection of the reference voltages.

Although the invention has been described in conjunction with an exemplary or illustrative embodiment, it should be appreciated that the invention is never restricted to the structure of the illustrated embodiment and various modifications will be readily thought of by those skilled in the art without departing from the spirit and scope of the present invention.

We claim:

1. An automatic cell sample classification apparatus comprising:
    loading means accommodating sample slides, each of which is randomly stained by one of plural different predetermined staining methods that differ from each other in at least the transmittance of light of a fixed wavelength;
    an examination station;
    means for extracting a given one of said sample slides sequentially from said loading means and transporting to said examination station along a predetermined path;
    light source means for transmitting light, including said fixed wavelength, through said given one of said sample slides;
    means disposed in a region located in the vicinity of said path, for producing a light intensity signal indicative of the luminous intensity of the light component at said fixed wavelengths that is transmitted through the given one of said sample slides;
    discriminating means for producing a discriminating signal based on said light intensity signal, said discriminating signal indicating the one of said plural staining methods by which the given one of said sample slides has been stained;
    means for obtaining a microscopic image of the cell sample of said given one of said sample slides;
    means for storing in a memory at least two different cell examination/classification programs associated respectively with two different ones of the plural predetermined staining methods;
    means for retrieving only one of said examination/classification programs from the memory in response to said discriminating signal indicating the staining method associated with said one of said examination/classification programs; and
    means for examining and classifying the cell sample of said given one of said sample slides by processing said microscopic image in accordance with said one of said examination/classification programs selected depending on said discriminating signal.

2. An automatic cell sample classification apparatus according to claim 1, wherein said light source means is disposed on one side of said transporting path for projecting light rays to said cell sample slide moving along said transporting means for producing a light intensity signal including a light receiving section disposed on the other side of said transporting path receiving light rays transmitted through said cell sample slide moving along said transporting path illuminated by said light source, said discriminating means having means for comparing said light intensity signal with at least one reference signal.

3. An automatic cell sample classification apparatus according to claim 2, wherein said means for comparing compares said discriminating based on said light intensity signal to a first reference signal corresponding to a transmitted light intensity level that is substantially lower than a light intensity signal corresponding to the presence of any one of the sample slides, to produce a first bit of a binary code corresponding to the respective absence or presence of a cell sample at said fixed wavelength; said means for further comparing compares said light intensity signal with a second reference signal substantially greater than any discriminating signal that would be produced by the absence of a blood sample cell and smaller than any transmittance signal that would be produced by a blood sample cell stained by one of said methods, to provide another bit of the binary code indicating the presence of a sample stained by a method other than said one of said methods at said fixed wavelength; and said means for further comparing compares said light intensity signal with a third reference signal that is greater than the light intensity signal that would be produced by any sample stained in accordance with said method other than said one of said methods and greater than the minimum light intensity signal that would be produced by any of said one of said methods at said fixed wavelength.

4. An automatic cell sample classification apparatus according to claim 1, wherein said means for obtaining the microscopic image includes means for obtaining red, green and blue color-separated signals representing the microscopic image of the cell sample contained in said sample slide placed in said examination station, said green color-separated signal being made use of as said light intensity signal.

5. The automatic cell sample classification apparatus according to claim 1 for classifying blood cells respectively stained by one of the staining methods of Romanowsky and Spravital, wherein said loading means accommodates and said means for extracting extracts the given one of said blood samples slides.

* * * * *